United States Patent [19]

Michelet et al.

[11] 4,256,647

[45] Mar. 17, 1981

[54] PROCESS FOR THE PREPARATION OF 2,3-DIHYDRO-2,2-DIMETHYL-7-HYDROXYBENZOFURANE

[75] Inventors: Daniel Michelet, Tassin la Demi Lune; Michel Rakoutz, Oullins, both of France

[73] Assignee: Philagro, Lyons, France

[21] Appl. No.: 95,445

[22] Filed: Nov. 19, 1979

[30] Foreign Application Priority Data

Nov. 30, 1978 [FR] France ............................... 78 34296
Jul. 18, 1979 [FR] France ............................... 79 19126

[51] Int. Cl.³ .................................................. C07B 307/86
[52] U.S. Cl. ............................................... 260/346.22
[58] Field of Search ........................ 260/346.22, 346.73

[56] References Cited

U.S. PATENT DOCUMENTS 3,455,961  7/1969  Weber, Jr. ..................... 260/346.22
3,474,171  10/1969  Scharpf ........................ 260/346.73
3,547,955  12/1970  Scharpf ........................ 260/346.22

FOREIGN PATENT DOCUMENTS 999128  7/1965  United Kingdom .
1179250  1/1970  United Kingdom .

*Primary Examiner*—Henry R. Jiles
*Assistant Examiner*—Bernard Dentz
*Attorney, Agent, or Firm*—Browdy and Neimark

[57] ABSTRACT

Process for the preparation of 2,3-dihydro-2,2-dimethyl-7-hydroxybenzofurane, a carbofuran intermediate, from methallylpyrocatechol comprises heating the methallylpyrocatechol in the presence of water and optionally also in the presence of an inert organic solvent having a boiling point above 70° C., the volume ratio of solvent to water being less than 3, the weight ratio of water to ortho-methallylpyrocatechol being between 0.3 and 5, and at a temperature of preferably 170°–230° C.

14 Claims, No Drawings

PROCESS FOR THE PREPARATION OF 2,3-DIHYDRO-2,2-DIMETHYL-7-HYDROXYBENZOFURANE

The invention relates to a process for the preparation of 2,3-dihydro-2,2-dimethyl-7-hydroxybenzofurane. This compound has the formula:

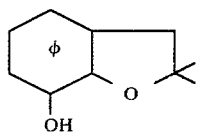

2,3-Dihydro-2,2-dimethyl-7-hydroxybenzofurane, hereafter designated by DDHB, is a compound which is in itself known and can be used for the preparation of 2,3-dihydro-2,2-dimethylbenzofuran-7-yl methylcarbamate which is a polyvalent insecticide known by the name carbofuran.

It is known from U.S. Pat. No. 3,474,171 that DDHB can be obtained from ortho-methallyloxyphenol by the rearrangement of this compound (ortho-transposition of the methallyl radical and cyclisation of the compound thus formed). According to such patent, DDHB is obtained by heating ortho-methallyloxyphenol in bulk without using a solvent or a diluent.

Ortho-methallyloxyphenol is the compound of the formula:

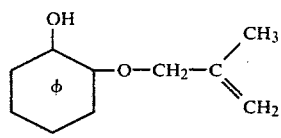

One object of the present invention is to provide an improved process for the preparation of DDHB, in particular from ortho-methallylpyrocatechol.

Another object of the invention is to prepare DDHB from ortho-methallyloxyphenol, with an improved yield.

Another object of the invention is to make it possible essentially to prepare DDHB from ortho-methallyloxyphenol in a single step, without it being necessary immediately to isolate the compound formed.

It has now been found that these objects can be achieved by virtue of a new process which forms the subject of the present invention.

This process is a process for the preparation of DDHB from ortho-methallylpyrocatechol, which comprises heating ortho-methallylpyrocatechol in the presence of liquid water and optionally in the presence of a (liquid) inert organic solvent.

The term "inert solvent" is understood as meaning a solvent which does not take part in a chemical reaction in the reaction medium and under the operating conditions.

In the present account, ortho-methallylpyrocatechol denotes the product of the formula:

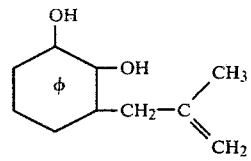

According to a variant of the invention, ortho-methallylpyrocatechol is prepared by heating ortho-methallyloxyphenol in the presence of water and/or in the presence of an inert organic solvent.

It follows that, in the case where ortho-methallyl-pyrocatechol is prepared by heating ortho-methallyloxyphenol in the presence of water, the process carried out (which forms part of the invention) consists in preparing DDHB (in a single step) by heating ortho-methallyloxyphenol in the presence of (liquid) water and optionally in the presence of a (liquid) inert organic solvent.

It also follows that, in the case where ortho-methallylpyrocatechol is prepared by heating ortho-methallyloxyphenol in the presence of a (liquid) inert organic solvent, the process carried out (which forms part of the invention) consists in preparing DDHB by heating ortho-methallyloxyphenol, and, during part of this heating period (when heating ends), the reaction medium contains (liquid) water and optionally a (liquid) inert organic solvent.

A particular subject of the invention is therefore a process for the preparation of DDHB from ortho-methallyloxyphenol, wherein ortho-methallyloxyphenol is heated and wherein, during all or part of this heating period, the reaction medium contains (liquid) water and optionally a (liquid) inert solvent. According to a particular embodiment of the invention, ortho-methallylpyrocatechol and/or ortho-methallyloxyphenol are simply heated in water, without using a solvent. According to another embodiment of the invention, these same reactions are carried out in the presence of water and a (liquid) inert organic solvent, i.e. a solvent which does not react chemically under the reaction conditions.

In the case where DDHB is prepared by heating ortho-methallylpyrocatechol in the presence of water, and where the ortho-methallylpyrocatechol has been prepared beforehand by heating ortho-methallyloxyphenol without using water, this latter reaction is carried out in the presence of an organic solvent. In other words, according to a variant of the invention in which DDHB is prepared from ortho-methallyloxyphenol, water is present in the reaction medium during the entire period of operation of the process of the invention; this variant therefore represents a process for the preparation of DDHB from ortho-methallyloxyphenol in the presence of water, this water being present as from the time when heating starts.

According to another variant of the invention in which DDHB is prepared from ortho-methallyloxyphenol, water is only introduced into the reaction medium when a certain heating period has elapsed, during which the ortho-methallyloxyphenol, heated in the absence of water and in the presence of an inert organic solvent, has been totally or partially converted to intermediates (in particular ortho-methallylpyrocatechol), and it is only after this first conversion that the reaction medium contains water, or in other words that the reaction medium is heated in the presence of water, or in other words that water is added to the reaction medium.

These intermediates are, in particular, one or more methallylpyrocatechols.

The relative proportion of water and organic solvent can vary within wide limits. Preferably, the volume ratio of the amount of organic solvent to the amount of water used is less than 3.

The amount of water employed, relative to the ortho-methallylpyrocatechol or to the ortho-methallyloxyphenol used in the reaction, is generally between 0.1 and 20 and preferably between 0.3 and 5 (ratio of amounts by weight).

The organic solvent can be either miscible with water or immiscible with water. The organic solvent which is preferably used is a solvent of high b.p., chosen from amongst aromatic hydrocarbons, such as toluene or o-, m- and p-xylenes, chlorinated aromatic hydrocarbons, such as chlorobenzene, aliphatic hydrocarbons, such as octane or dodecane, chlorinated aliphatic hydrocarbons, such as 1,2-dichloroethane or 1,1,2-trichloroethane, cycloaliphatic hydrocarbons, such as cyclohexane or methylcyclohexane, aromatic ethers, such as anisole, ketones, such as methyl isobutyl ketone, and nitriles, such as acetonitrile or adiponitrile.

The term "solvent of high b.p." is understood as meaning a solvent having a b.p. above 70° C. and preferably equal to at least 80° C.

The temperature at which the ortho-methallylpyrocatechol or the ortho-methallyloxyphenol is heated, in accordance with the process, must be high enough to permit the conversion of the ortho-methallylpyrocatechol or the ortho-methallyloxyphenol into DDHB. However, in order to prevent the thermal degradation of the DDHB formed, it must not be too high. This temperature is advantageously between 100° and 250° C. and preferably between 170° and 230° C. So that the water and/or the organic solvent are liquid, the reaction is preferably carried out under a sufficient pressure to bring the constituents present in the reaction medium into liquid form.

The period required to convert the ortho-methallylpyrocatechol or the ortho-methallyloxyphenol into DDHB, according to the invention, depends on the temperature used, i.e. this period is shorter, the higher is the temperature. This period is advantageously between one hour and four hours.

At the end of the reaction, the DDHB obtained is separated off by any means which is in itself known, such as e.g. by distillation. However, for certain uses, it may not be necessary to isolate the DDHB and it then suffices to leave it in the reaction medium which is itself employed in the desired manner.

Ortho-methallyloxyphenol is a compound which is in itself known, the preparation of which has been described in U.S. Pat. No. 3,927,118.

The following examples, which are given without implying a limitation, illustrate the invention and show how it can be put into effect.

EXAMPLE 1

Ortho-methallyloxyphenol (1.50 g), dodecane (15 cc) and water (10 cc) are introduced into an autoclave. The autoclave is purged with argon, heated at 200° C. for 2 hours 45 minutes and then allowed to cool. The autoclave is then emptied and rinsed with ethyl acetate (10 cc) which is combined with the crude reaction mixture. The resulting mixture is separated by decantation and the aqueous phase is extracted with ethyl acetate (2×5 cc). These extracts are combined with the decanted organic phase, and DDHB (1.075 g) is determined in the resulting mixture by chromatographic analysis; furthermore, it is observed that the reaction mixture no longer contains any ortho-methallyloxyphenol.

Expressed in percent, the results are as follows:
degree of conversion of the ortho-methallyloxyphenol employed: 100%
molar yield of DDHB, relative to the ortho-methallyloxyphenol: 71.6%.

EXAMPLES 2 to 4

The procedure of Example 1 is followed, but the amount of ortho-methallyloxyphenol used, the reaction medium and the heating period and temperature are varied.

The results observed are recorded in the table below, in which the following terms have the following meanings respectively:
Monoether: amount of ortho-methallyloxyphenol used
DDHB: amount of 2,3-dihydro-2,2-dimethyl-7-hydroxybenzofurane obtained
Yield (DDHB): molar yield of DDHB, relative to the ortho-methallyloxyphenol.

The degree of conversion of the ortho-methallyloxyphenol in these examples was equal or virtually equal to 100%.

EXAMPLE 5

Ortho-methallyloxyphenol (1.1018 g) and cyclohexane (10 cc) are introduced into a titanium autoclave (50 cc). The autoclave is heated for 1 hour 30 minutes at 200° C. and then cooled. Analysis then shows that the ortho-methallyloxyphenol has disappeared from the reaction medium and that predominantly methylpyrocatechols have been formed.

Water (5 cc) is added and the autoclave is then heated again at 200° C. for 1 hour 30 minutes and then cooled; DDHB was obtained with a yield of 70.5%, relative to the ortho-methallyloxyphenol employed.

| Example | Monoether (in g) | Reaction medium | Heating temperature | period | DDHB in g | Yield (DDHB) |
|---|---|---|---|---|---|---|
| 2 | 1.473 | Dodecane (15 cc) Water (10 cc) | 200° C. | 2 hours | 1.044 | 71.3% |
| 3 | 3.0 | Water (9 cc) | 200° C. | 1 hour 25 minutes | 2.075 | 69.1% |
| 4 | 1.50 | Toluene (15 cc) Water (10 cc) | 200° C. | 2 hours | 1.081 | 72.1% |

We claim:
1. In a process for the preparation of 2,3-dihydro-2,2-dimethyl-7-hydroxybenzofurane comprising heating a starting reagent of ortho-metallylpyrocatechol to effect the cyclization thereof, the improvement wherein said heating is carried out in the presence of water in the liquid phase in an amount sufficient to increase the yield of 2,3-dihydro-2,2-dimethyl-7-hydroxybenzofurane.

2. In a process for the preparation of 2,3-dihydro-2,2-dimethyl-7-hydroxybenzofurane comprising heating a starting reagent of ortho-metallyloxyphenol to effect rearrangement and cyclization thereof, the improvement wherein said heating is carried out in the presence of water in the liquid phase in an amount sufficient to increase the yield of 2,3-dihydro-2,2-dimethyl-7-hydroxybenzofurane.

3. A process for the preparation of 2,3-dihydro-2,2-dimethyl-7-hydroxybenzofurane, which comprises heating ortho-methallyloxyphenol in the absence of water and in the presence of an inert organic solvent, and then subsequently continuing heating in the presence of water.

4. A process according to one of claims 3, 1 or 2 wherein said liquid water is present in a quantity by weight of between 0.1 and 20 parts based on the weight of said ortho-methallylpyrocatechol or ortho-methallyloxyphenol.

5. A process according to claim 1 or 2, wherein heating is also carried out in the presence of an inert organic solvent.

6. A process according to claim 5, wherein the organic solvent has a b.p. above 70° C.

7. A process according to claim 5, wherein the volume ratio solvent/water employed is less than 3.

8. A process according to claim 4, wherein the weight ratio water/ortho-methallyloxyphenol or ortho-methallylpyrocatechol used is between 0.3 and 5.

9. A process according to claim 3 wherein the organic solvent has a B.P. above 70° C.

10. A process according to claim 3 wherein the volume ratio solvent/water employed is less than 3.

11. A process according to claim 6 or 9, wherein the organic solvent is an aromatic hydrocarbon, an aliphatic hydrocarbon, a cycloaliphatic hydrocarbon, a ketone, a nitrile or an alcohol.

12. A process according to claim 11, wherein the solvent is octane, dodecane, methylcyclohexane, cyclohexane, toluene, xylenes or methyl isobutyl ketone.

13. A process according to one of claims 3, 1 or 2, wherein the reaction temperature is between 100° and 250° C.

14. A process according to claim 13, wherein the reaction temperature is between 170° and 230° C.

* * * * *